US008552155B2

(12) United States Patent
Lipinski et al.

(10) Patent No.: US 8,552,155 B2
(45) Date of Patent: Oct. 8, 2013

(54) ANTI-PYK2 ANTIBODIES

(75) Inventors: Christopher A. Lipinski, Scottsdale, AZ (US); Joseph C. Loftus, Scottsdale, AZ (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 192 days.

(21) Appl. No.: 12/994,535

(22) PCT Filed: May 28, 2009

(86) PCT No.: PCT/US2009/045495
§ 371 (c)(1),
(2), (4) Date: Feb. 18, 2011

(87) PCT Pub. No.: WO2009/155060
PCT Pub. Date: Dec. 23, 2009

(65) Prior Publication Data
US 2011/0136232 A1    Jun. 9, 2011

Related U.S. Application Data

(60) Provisional application No. 61/056,727, filed on May 28, 2008.

(51) Int. Cl.
*C07K 16/00* (2006.01)
(52) U.S. Cl.
USPC ..................... 530/387.7; 530/387.1
(58) Field of Classification Search
None
See application file for complete search history.

(56) References Cited

U.S. PATENT DOCUMENTS

| 4,036,945 | A | 7/1977 | Haber |
| 4,331,647 | A | 5/1982 | Goldenberg |
| 2003/0119067 | A1* | 6/2003 | Lev et al. ............ 435/7.1 |
| 2004/0005648 | A1* | 1/2004 | Lev et al. ............ 435/7.23 |

FOREIGN PATENT DOCUMENTS

WO    WO 91/11465    8/1991

OTHER PUBLICATIONS

Campbell, Monoclonal Antibody Technology eds. Elseivers, 1984, Chapter 1, pp. 1-32.*
Kohno, Biochem. J. vol. 410 p. 513 (2008).*
Andreev et al., "Identification of a New Pyk2 Target Protein with Arf-GAP Activity," *Mol Cell Biol.*, 1999, 19(3):2338-50.
Avraham et al., "RAFTK/Pyk2-mediated cellular signaling," *Cell Signal*, 2000, 12(3):123-33.
Avraham et al., "Identification and Characterization of a Novel Related Adhesion Focal Tyrosine Kinase (RAFTK) from Megakaryocytes and Brain," *J. Biol. Chem.*, 1995, 270(46):27742-51.
Barbas et al., "Combinatorial Immunoglobulin Libraries on the Surgace of Phage (Phabs): Rapid Selection of Antigen-Specific Fabs," *Method: A Companion to Methods in Enzymology*, 1991, 2: 119-124.
Baines and Thorpe, "Purification of Immunoglobulin G (IgG)," *Methods in Molecular Biology*, 1992, 10:79-104.
Carter et al., "Humanization of an anti-p185$^{HER2}$ antibody for human cancer therapy," *Proc. Nat'l. Acad. Sci. USA*, 1992, 89:4285-4289.
Coligan et al., *Current Protocols in Immunology*, 1992, Unit 2.0-2.10, 29 pages.
Coligan et al., *Current Protocols in Immunology*, 1994, Unit 9, 4 pages (Table of Contents and Introduction).
de Pereda et at., "Crystal Structure of a Human Peptidyl-tRNA Hydrolase Reveals a New Fold and Suggests Basis for a Bifunctional Activity," *J. Biol.Chem.*, 2004, 279:8111-8115.
Edelman et al., *Methods in Enzymology*, 1967, 1:422.
Garcia-Alvarez et al., "Structural Determinants of Integrin Recognition by Talin," *Mol. Cell.*, 2003, 11:49-58.
Gene Therapy Protocols, *Methods in Molecular Medicine*, edited by Jeffrey R. Morgan, Humana Press, Totowa, NJ, 2002, 3 pages, (Table of Contents).
Giannini et al., "Patient tumor *EGFR* and *PDGFRA* gene amplifications retained in an invasive intracranial xenograft model of glioblastoma multiforme," *Neuro-Oncol.*, 2005, 7:164-76.
Giese et al., "Determinants of Human Astrocytoma Migration," *Cancer Res.*, 1994, 54:3897-904.
Green et al., "Antigen-specific human monoclonal antibodies from mice engineered with human Ig heavy and light chain YAC," *Nature Genet.*, 1994, 7:13-21.
Green and Manson,"Production of Polyclonal Antisera," in *Immunochemical Protocols*, 1992, pp. 1-5.
Gutenberg et al., "Expression of tyrosine kinases FAK and Pyk2 in 331 human astrocytomas," *Acta Neuropathol.*, 2004, 108(3):224-30.
Hamada et al., "Structural basis of adhesion-molecule recognition by ERM proteins revealed by the crystal structure of the radixin-iCAM-2 complex," *EMBO J.*, 2003, 22:502-514.
Harlow et al., *Antibodies: A Laboratory Manual*, 1988, 10 pages (Table of Contents).
Hoelzinger et al., "Gene expression profile of glioblastoma multiformes invasive phenotype points to new therapeutic targets," *Neoplasia*, 2005, 7(1):7-16.
Jones et at., "Replacing the complementarity determining regions in a human antibody with those from a mouse," *Nature*, 1986, 321:522-525.
Kohler & Milstein, "Continuous cultures of fused cells secreting antibody of predefined specificity," *Nature*, 1975, 256:495-497.
Kruljac-Letunic et al., "The Tyrosine Kinase Pyk2 Regulates Arfl Activity by Phosphyorylation and Inhibition of the Arf-GTPase-activating Protein ASAP1," *J. Biol. Chem.*, 2003, 278(32):29560-70.
Lipinski et al., "Critical role of the FERM domain in Pyk2 stimulated glioma cell migration," Biochem. *Biophys. Res. Commun.*, 2006, 349:939-947.

(Continued)

*Primary Examiner* — Sheela J Huff
(74) *Attorney, Agent, or Firm* — Fish & Richardson P.C.

(57) ABSTRACT

This document provides methods and materials related to anti-Pyk2 antibodies. For example, anti-Pyk2 antibodies, methods for making anti-Pyk2 antibodies, and methods for using an anti-Pyk2 antibody to inhibit glioma cell migration are provided.

11 Claims, 11 Drawing Sheets

(56) References Cited

OTHER PUBLICATIONS

Lipinski et al., "Differential Role of Proline-Rich Tyrosine Kinase 2 and Focal Adhesion Kinase in Determining Glioblastoma Migration and Proliferation," *Mol. Cancer Res.*, 2003, 1:323-332.

Lipinski et al., "The Tyrosine Kinase Pyk2 Promotes Migration and Invasion of Glioma Cells," *Neoplasia*, 2005, 7:435-445.

Lipinski et al., "Extended survival of Pyk2 or FAK deficient orthotopic glioma xenografts," *J. Neurooncology*, 2008, 90:181-189 (Author Manuscript).

Lonberg et al., "Antigen-specific human antibodies from mice comprising four distinct genetic modifications," *Nature*, 1994, 368:856-859.

Losman et al., "Baboon Anti-Idiotype Antibodies Mimic a Carcinoembryonic Antigen Epitope," *Int. J. Cancer*, 1990, 46:310-314.

Nakamura et al., "Different modes and qualities of tyrosine phosphorylation of Fak and Pyk2 during epithelial-mesenchymal transdifferentiation and cell migration:analysis of specific phosphorylation events using site-directed antibodies," *Oncogene*, 2001, 20:2626-2635.

Nisonhoff et al., "Separation of Univalent Fragments from the Bivalent Rabbit Antibody Molecule by Reduction of Disulfide Bonds," *Arch. Biochem. Biophys.*, 1960, 89:230-244.

Orlandi et al., "Cloning immunoglobulin variable domains for expression by the polymerase chain reaction," *Proc. Nat'l. Acad. Sci. USA*, 1989, 86:3833-3837.

Park et al., "RAFTK/Pyk2 Activation is Mediated by Trans-acting Autophosphorylation in a Src-independent Manner," *J Biol. Chem.*, 2004, 279:33315-22.

Porter, "The Hydrolysis of Rabbit γ-Globulin and Antibodies with Crystalline Papain," *Biochem. J.*, 1959, 73:119-126.

Ren et al., "Regulation of Cdc42 Gtpase by Proline-Rich Tyrosine Kinase 2 Interacting with Psgap, a Novel Pleckstrin Homology 3 Domain Containing Rhogap Protein," *J. Cell. Biol.*, 2001, 152(5):971-84.

Riechmann et al., "Reshaping human anitbodies for therapy," *Nature*, 1988, 332:323-237.

Sandhu, "Protein Engineering of Antibodies," *Crit. Rev. Biotech.*, 1992, 12:437-462.

Sasaki et al., "Cloning and Characterization of Cell Adhesion Kinase β, a Novel Protein-tyrosine Kinase of the Focal Adhesion Kinase Subfamily," *J. Biol. Chem.*, 1995, 270(36):21206-19.

Singer et al., "Optimal Humanization of 1B4, an Anti-CD18 Murine Monoclonal Antibody, is Achieved by Correct Choice of Human V-Region Framework Sequences," *J Immunol.*, 1993, 150:2844-2587.

Taylor et al., "Human immunoglobulin transgene undergo rearrangement, somatic mutation and class switching in mice that lack endogenous IgM," *Int. Immunol.*, 1994, 6:579-591.

Verhoeyen et al., "Reshaping Human Antibodies: Grafting an Antilysozyme Activity," *Science*, 1988, 239:1534-1536.

*Viral Vectors for Gene Therapy: Methods and Protocols*, edited by Curtis A. Machida, Humana Press, Totowa, NJ, 2003, 6 pages (Table of Contents).

Wang et al., "Universal PCR amplification of mouse immunoglobulin gene variable regions: the design of degenerate primers and an assessment of the effect of DNA polymerase 3' to 5' exonuclease activity," *J Immunol. Methods*, 2000, 233:167-177.

Winter et al., "Making Antibodies by Phage Display Technology," *Ann. Rev. Immunol.*, 1994, 12:433-455.

Wiznerowicz & Trono, "Conditional Suppression of Cellular Genes: Lentivirus Vector-Mediated Drug-Inducible RNA Interference," *J Virol.*, 2003, 77:8957-8961.

Wu, "Differential regulation of Pyk2 phosphorylation at Tyr-402 and Try-580 in intestinal epithelial cells: roles of calcium, Src, Rho kinase and the cytoskeleton," *Cellular Signalling*, 2006,18:1932-1940.

Zrihan-Licht et al., "Coupling of RAFTK/Pyk2 kinase with c-Abl and their role in the migration of breast cancer cells," *Int. J. Oncol.*, 2004, 24(I):153-9.

International Search Report and Written Opinion in International Application No. PCT/US2009/045495, mailed Jan. 27, 2010, 13 pages.

International Preliminary Report on Patentability in International Application No. PCT/US2009/045495, mailed Dec. 9, 2010, 6 pages.

* cited by examiner

VH

| | | | | | | | | | | | | | | | | |
|---|---|---|---|---|---|---|---|---|---|---|---|---|---|---|---|---|
| ATG | GAG | GTA | AAG | CTG | CAG | GAG | TCT | GGA | CCT | GAG | CTG | AAG | AAG | CCT | GGA | GAG | ACA | GTC | AAA |
| M | E | V | K | L | Q | E | S | G | P | E | L | K | K | P | G | E | T | V | K |

```
ATG GAG GTA AAG CTG CAG GAG TCT GGA CCT GAG CTG AAG AAG CCT GGA GAG ACA GTC AAA
 M   E   V   K   L   Q   E   S   G   P   E   L   K   K   P   G   E   T   V   K

ATC TCC TGC AAG GCC TCT GGT TAT ACC TTC ACA GAC TAT TCA ATG CAC TGG GTG ATG CAG
 I   S   C   K   A   S   G   *Y*  *T*  *F*  *T*  *D*  *Y*  *S*  *M*  *H*  W   V   M   Q

TCT CCA GGA AAG GGT TTA AAG TGG ATG GGC TGG ATA AAC ACT GAG ACT GGT GAG CCT AGA
 S   P   G   K   G   L   K   W   M   G   *W*  *I*  *N*  *T*  *E*  *T*  *G*  *E*  *P*  *R*

TAT GTT GAT GAC TTC AAG GGG CGG TTT GCC TTC TCT TTG GAA ACC TCT GCC AGC ACT GCC
 *Y*  *V*  *D*  *D*  *F*  *K*  *G*  R   F   A   F   S   L   E   T   S   A   S   T   A

TAT TTG CAG ATC ATC AAT CTC AAA AAT GAG GAC ACG GCT ACA TAT TTC TGC GCT AGA TGG
 Y   L   Q   I   I   N   L   K   N   E   D   T   A   T   Y   F   C   A   R   *W*

GAC CAC GGC CAC GGG GGG TTT ACT TAC TGG GGC CAA GGG ACT CTG GTC ACT GTC TCT GCA
 *D*  *H*  *G*  *H*  *G*  *G*  *F*  *T*  *Y*  W   G   Q   G   T   L   V   T   V   S   A
                                                                                  VL
GGT GGC GGT GGC TCG GGC GGT GGT GGG TCG GGT GGC GGC GGA TCG GAT ATT GTG CTG ACA
 G   G   G   G   S   G   G   G   G   S   G   G   G   G   S   D   I   V   L   T

CAA ACT ACA GCT TCT TTG GCT GTG TCT CTA GGG CAG AGG GCC ACC ATG TCC TGC AGA GCC
 Q   T   T   A   S   L   A   V   S   L   G   Q   R   A   T   M   S   C   *R*  *A*

ACT GAA AGT GTT GAT AGT TAT GGC AAA AGT TTT ATG TAC TGG TTC CAG CAG AGA GCA GGA
 *T*  *E*  *S*  *V*  *D*  *S*  *Y*  *G*  *K*  *S*  *F*  *M*  *Y*  W   F   Q   Q   R   A   G

CAG CCA CCC AAA CTC CTC ATC TAC CTT GCA TCC AAC CTA GAA TCT GTG GTC CCT CCC AGG
 Q   P   P   K   L   L   I   Y   *L*  *A*  *S*  *N*  *L*  *E*  *S*  V   V   P   P   R

TTC AGT GGC AGT GGG TCT AGG ACA GAC TTC TCC CTC ACC ATT GAT CCT GTG GAG GCT GAT
 F   S   G   S   G   S   R   T   D   F   S   L   T   I   D   P   V   E   A   D

GAT GCT GCA ACC TAT TAC TGT CAA CAA AAT AAT GAG GAT CCA TTC ACG TTC GGC TCG GGG
 D   A   A   T   Y   Y   C   *Q*  *Q*  *N*  *N*  *E*  *D*  *P*  *F*  *T*  *F*  G   S   G

ACA AAG TTG GAA ATA AAA ctc gag
 T   K   L   E   I   K
```

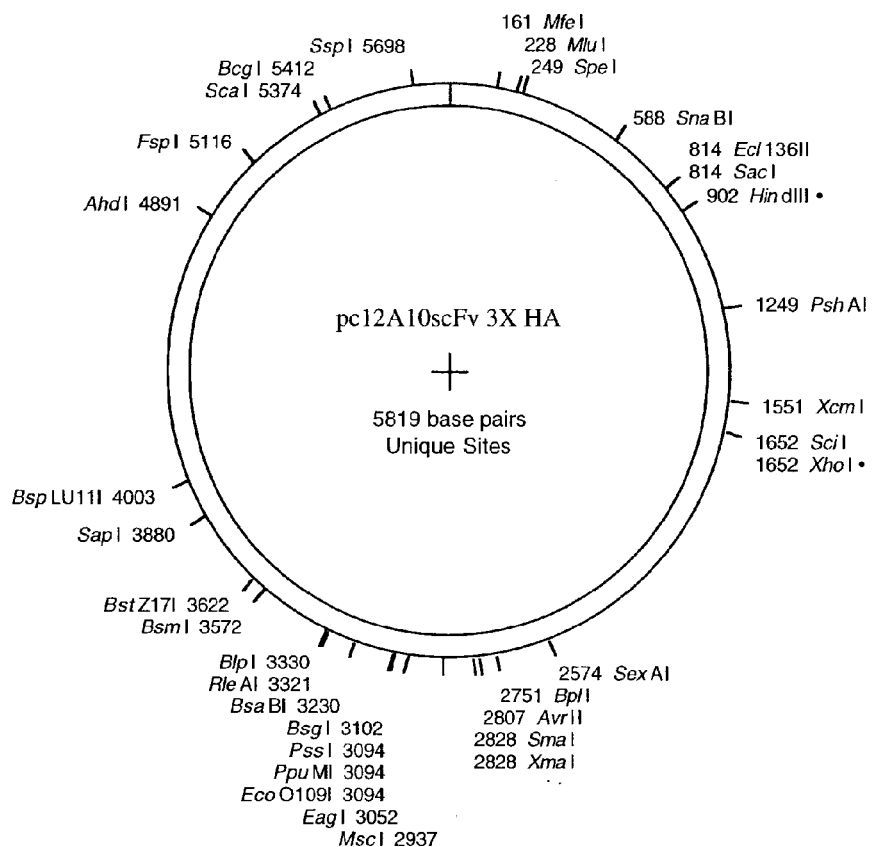

GACGGATCGGGAGATCTCCCGATCCCCTATGGTGCACTCTCAGTACAATC
TGCTCTGATGCCGCATAGTTAAGCCAGTATCTGCTCCCTGCTTGTGTGTT
GGAGGTCGCTGAGTAGTGCGCGAGCAAAATTTAAGCTACAACAAGGCAAG
GCTTGACCGACAATTGCATGAAGAATCTGCTTAGGGTTAGGCGTTTTGCG
CTGCTTCGCGATGTACGGGCCAGATATACGCGTTGACATTGATTATTGAC
TAGTTATTAATAGTAATCAATTACGGGGTCATTAGTTCATAGCCCATATA
TGGAGTTCCGCGTTACATAACTTACGGTAAATGGCCCGCCTGGCTGACCG
CCCAACGACCCCCGCCCATTGACGTCAATAATGACGTATGTTCCCATAGT
AACGCCAATAGGGACTTTCCATTGACGTCAATGGGTGGAGTATTTACGGT
AAACTGCCCACTTGGCAGTACATCAAGTGTATCATATGCCAAGTACGCCC
CCTATTGACGTCAATGACGGTAAATGGCCCGCCTGGCATTATGCCCAGTA
CATGACCTTATGGGACTTTCCTACTTGGCAGTACATCTACGTATTAGTCA
TCGCTATTACCATGGTGATGCGGTTTTGGCAGTACATCAATGGGCGTGGA
TAGCGGTTTGACTCACGGGGATTTCCAAGTCTCCACCCCATTGACGTCAA

FIGURE 8 continued

```
TGGGAGTTTGTTTTGGCACCAAAATCAACGGGACTTTCCAAAATGTCGTA
ACAACTCCGCCCCATTGACGCAAATGGGCGGTAGGCGTGTACGGTGGGAG
GTCTATATAAGCAGAGCTCTCTGGCTAACTAGAGAACCCACTGCTTACTG
GCTTATCGAAATTAATACGACTCACTATAGGGAGACCCAAGCTGGCTAGT
Taagcttacc ATGGAGGTAAAGCTGCAGGAGTCTGGACCTGAGCTGAAGA ⎫
AGCCTGGAGAGACAGTCAAGATCTCCTGCAAGGCCTCTGGTTATACCTTC  ⎪
ACAGACTATTCAATGCACTGGGTGATGCAGTCTCCAGGAAAGGGTTTAAA  ⎪
GTGGATGGGCTGGATAAACACTGAGACTGGTGAGCCTAGATATGTTGATG  ⎬ Vн
ACTTCAAGGGGCGGTTTGCCTTCTCTTTGGAAACCTCTGCCAGCACTGCC  ⎪
TATTTGCAGATCATCAATCTCAAAAATGAGGACACGGCTACATATTTCTG  ⎪
CGCTAGATGGGACCACGGCCACGGGGGGTTTACTTACTGGGGCCAAGGGA ⎭
CTCTGGTCACTGTCTCTGCAGCC ggtggcggtggctcgggcggtggtggg — Linker
tcgggtggcggcggatcg GATATTGTGCTGACACAAACTACAGCTTCTTT ⎫
GGCTGTGTCTCTAGGGCAGAGGGCCACCATGTCCTGCAGAGCCACTGAAA  ⎪
GTGTTGATAGTTATGGCAAAAGTTTTATGTACTGGTTCCAGCAGAGAGCA  ⎪
GGACAGCCACCCAAACTCCTCATCTACCTTGCATCCAACCTAGAATCTGT  ⎬ Vʟ
GGTCCCTCCCAGGTTCAGTGGCAGTGGGTCTAGGACAGACTTCTCCCTCA  ⎪
CCATTGATCCTGTGGAGGCTGATGATGCTGCAACCTATTACTGTCAACAA  ⎪
AATAATGAGGATCCATTCACGTTCGGCTCGGGGACAAAGTTGGAAATAAA ⎭
Actcgagggatcttacccatacgatgttcctgactatgcgggctatccct
atgacgtcccggactatgcaggatcctatccatatgacgttccagattac
gctTAGgataaacCCGCTGATCAGCCTCGACTGTGCCTTCTAGTTGCCAG
CCATCTGTTGTTTGCCCCTCCCCGTGCCTTCCTTGACCCTGGAAGGTGC
CACTCCCACTGTCCTTTCCTAATAAAATGAGGAAATTGCATCGCATTGTC
TGAGTAGGTGTCATTCTATTCTGGGGGGTGGGGTGGGCAGGACAGCAAG
GGGGAGGATTGGGAAGACAATAGCAGGCATGCTGGGGATGCGGTGGGCTC
TATGGCTTCTGAGGCGGAAAGAACCAGCTGGGGCTCTAGGGGTATCCCC
ACGCGCCCTGTAGCGGCGCATTAAGCGCGGCGGGTGTGGTGGTTACGCGC
AGCGTGACCGCTACACTTGCCAGCGCCCTAGCGCCCGCTCCTTTCGCTTT
CTTCCCTTCCTTTCTCGCCACGTTCGCCGGCTTTCCCCGTCAAGCTCTAA
ATCGGGGGCTCCCTTTAGGGTTCCGATTTAGTGCTTTACGGCACCTCGAC
CCCAAAAAACTTGATTAGGGTGATGGTTCACGTAGTGGGCCATCGCCCTG
ATAGACGGTTTTTCGCCCTTTGACGTTGGAGTCCACGTTCTTTAATAGTG
GACTCTTGTTCCAAACTGGAACAACACTCAACCCTATCTCGGTCTATTCT
TTTGATTTATAAGGGATTTTGCCGATTTCGGCCTATTGGTTAAAAAATGA
GCTGATTTAACAAAAATTTAACGCGAATTAATTCTGTGGAATGTGTGTCA
GTTAGGGTGTGGAAAGTCCCCAGGCTCCCCAGCAGGCAGAAGTATGCAAA
GCATGCATCTCAATTAGTCAGCAACCAGGTGTGGAAAGTCCCCAGGCTCC
CCAGCAGGCAGAAGTATGCAAAGCATGCATCTCAATTAGTCAGCAACCAT
AGTCCCGCCCCTAACTCCGCCCATCCCGCCCCTAACTCCGCCCAGTTCCG
CCCATTCTCCGCCCCATGGCTGACTAATTTTTTTTATTTATGCAGAGGCC
GAGGCCGCCTCTGCCTCTGAGCTATTCCAGAAGTAGTGAGGAGGCTTTTT
TGGAGGCCTAGGCTTTTGCAAAAAGCTCCCGGGAGCTTGTATATCCATTT
TCGGATCTGATCAGCACGTGTTGACAATTAATCATCGGCATAGTATATCG
GCATAGTATAATACGACAAGGTGAGGAACTAAACCATGGCCAAGCCTTTG
TCTCAAGAAGAATCCACCCTCATTGAAAGAGCAACGGCTACAATCAACAG
CATCCCCATCTCTGAAGACTACAGCGTCGCCAGCGCAGCTCTCTCTAGCG
ACGGCCGCATCTTCACTGGTGTCAATGTATATCATTTTACTGGGGGACCT
TGTGCAGAACTCGTGGTGCTGGGCACTGCTGCTGCTGCGGCAGCTGGCAA
CCTGACTTGTATCGTCGCGATCGGAAATGAGAACAGGGGCATCTTGAGCC
CCTGCGGACGGTGCCGACAGGTGCTTCTCGATCTGCATCCTGGGATCAAA
GCCATAGTGAAGGACAGTGATGGACAGCCGACGGCAGTTGGGATTCGTGA
ATTGCTGCCCTCTGGTTATGTGTGGGAGGGCTAAGCACTTCGTGGCCGAG
GAGCAGGACTGACACGTGCTACGAGATTTCGATTCCACCGCCGCCTTCTA
```

FIGURE 8 continued

```
TGAAAGGTTGGGCTTCGGAATCGTTTTCCGGGACGCCGGCTGGATGATCC
TCCAGCGCGGGGATCTCATGCTGGAGTTCTTCGCCCACCCCAACTTGTTT
ATTGCAGCTTATAATGGTTACAAATAAAGCAATAGCATCACAAATTTCAC
AAATAAAGCATTTTTTTCACTGCATTCTAGTTGTGGTTTGTCCAAACTCA
TCAATGTATCTTATCATGTCTGTATACCGTCGACCTCTAGCTAGAGCTTG
GCGTAATCATGGTCATAGCTGTTTCCTGTGTGAAATTGTTATCCGCTCAC
AATTCCACACAACATACGAGCCGGAAGCATAAAGTGTAAAGCCTGGGGTG
CCTAATGAGTGAGCTAACTCACATTAATTGCGTTGCGCTCACTGCCCGCT
TTCCAGTCGGGAAACCTGTCGTGCCAGCTGCATTAATGAATCGGCCAACG
CGCGGGGAGAGGCGGTTTGCGTATTGGGCGCTCTTCCGCTTCCTCGCTCA
CTGACTCGCTGCGCTCGGTCGTTCGGCTGCGGCGAGCGGTATCAGCTCAC
TCAAAGGCGGTAATACGGTTATCCACAGAATCAGGGGATAACGCAGGAAA
GAACATGTGAGCAAAAGGCCAGCAAAAGGCCAGGAACCGTAAAAAGGCCG
CGTTGCTGGCGTTTTTCCATAGGCTCCGCCCCCTGACGAGCATCACAAA
AATCGACGCTCAAGTCAGAGGTGGCGAAACCCGACAGGACTATAAAGATA
CCAGGCGTTTCCCCCTGGAAGCTCCCTCGTGCGCTCTCCTGTTCCGACCC
TGCCGCTTACCGGATACCTGTCCGCCTTTCTCCCTTCGGGAAGCGTGGCG
CTTTCTCATAGCTCACGCTGTAGGTATCTCAGTTCGGTGTAGGTCGTTCG
CTCCAAGCTGGGCTGTGTGCACGAACCCCCCGTTCAGCCCGACCGCTGCG
CCTTATCCGGTAACTATCGTCTTGAGTCCAACCCGGTAAGACACGACTTA
TCGCCACTGGCAGCAGCCACTGGTAACAGGATTAGCAGAGCGAGGTATGT
AGGCGGTGCTACAGAGTTCTTGAAGTGGTGGCCTAACTACGGCTACACTA
GAAGAACAGTATTTGGTATCTGCGCTCTGCTGAAGCCAGTTACCTTCGGA
AAAAGAGTTGGTAGCTCTTGATCCGGCAAACAAACCACCGCTGGTAGCGG
TGGTTTTTTTGTTTGCAAGCAGCAGATTACGCGCAGAAAAAAAGGATCTC
AAGAAGATCCTTTGATCTTTTCTACGGGGTCTGACGCTCAGTGGAACGAA
AACTCACGTTAAGGGATTTTGGTCATGAGATTATCAAAAAGGATCTTCAC
CTAGATCCTTTTAAATTAAAAATGAAGTTTTAAATCAATCTAAAGTATAT
ATGAGTAAACTTGGTCTGACAGTTACCAATGCTTAATCAGTGAGGCACCT
ATCTCAGCGATCTGTCTATTTCGTTCATCCATAGTTGCCTGACTCCCCGT
CGTGTAGATAACTACGATACGGGAGGGCTTACCATCTGGCCCCAGTGCTG
CAATGATACCGCGAGACCCACGCTCACCGGCTCCAGATTTATCAGCAATA
AACCAGCCAGCCGGAAGGGCCGAGCGCAGAAGTGGTCCTGCAACTTTATC
CGCCTCCATCCAGTCTATTAATTGTTGCCGGGAAGCTAGAGTAAGTAGTT
CGCCAGTTAATAGTTTGCGCAACGTTGTTGCCATTGCTACAGGCATCGTG
GTGTCACGCTCGTCGTTTGGTATGGCTTCATTCAGCTCCGGTTCCCAACG
ATCAAGGCGAGTTACATGATCCCCATGTTGTGCAAAAAAGCGGTTAGCT
CCTTCGGTCCTCCGATCGTTGTCAGAAGTAAGTTGGCCGCAGTGTTATCA
CTCATGGTTATGGCAGCACTGCATAATTCTCTTACTGTCATGCCATCCGT
AAGATGCTTTTCTGTGACTGGTGAGTACTCAACCAAGTCATTCTGAGAAT
AGTGTATGCGGCGACCGAGTTGCTCTTGCCCGGCGTCAATACGGGATAAT
ACCGCGCCACATAGCAGAACTTTAAAAGTGCTCATCATTGGAAAACGTTC
TTCGGGGCGAAAACTCTCAAGGATCTTACCGCTGTTGAGATCCAGTTCGA
TGTAACCCACTCGTGCACCCAACTGATCTTCAGCATCTTTTACTTTCACC
AGCGTTTCTGGGTGAGCAAAAACAGGAAGGCAAAATGCCGCAAAAAGGG
AATAAGGGCGACACGGAAATGTTGAATACTCATACTCTTCCTTTTTCAAT
ATTATTGAAGCATTTATCAGGGTTATTGTCTCATGAGCGGATACATATTT
GAATGTATTTAGAAAAATAAACAAATAGGGGTTCCGCGCACATTTCCCCG
AAAAGTGCCACCTGACGTC
```

FIGURE 9

Translated sequence of the 12A10 scFv

MEVKLQESGPELKKPGETVKISCKASGYTFTDYSMHWVMQSPGKGLKWMG
WINTETGEPRYVDDFKGRFAFSLETSASTAYLQIINLKNEDTATYFCARW
DHGHGGFTYWGQGTLVTVSAAGGGGSGGGGSGGGGSDIVLTQTTASLAVS
LGQRATMSCRATESVDSYGKSFMYWFQQRAGQPPKLLIYLASNLESVVPP
RFSGSGSRTDFSLTIDPVEADDAATYYCQQNNEDPFTFGSGTKLEIKLEG
SYPYDVPDYAGYPYDVPDYAGSYPYDVPDYAAQCGR*

SEQUENCE LISTING

<160> NUMBER OF SEQ ID NOS: 5

<210> SEQ ID NO 1
<211> LENGTH: 246
<212> TYPE: PRT
<213> ORGANISM: Artificial Sequence
<220> FEATURE:
<223> OTHER INFORMATION: Single chain antibody

<400> SEQUENCE: 1

```
Met Glu Val Lys Leu Gln Glu Ser Gly Pro Glu Leu Lys Lys Pro Gly
 1               5                  10                  15

Glu Thr Val Lys Ile Ser Cys Lys Ala Ser Gly Tyr Thr Phe Thr Asp
            20                  25                  30

Tyr Ser Met His Trp Val Met Gln Ser Pro Gly Lys Gly Leu Lys Trp
        35                  40                  45

Met Gly Trp Ile Asn Thr Glu Thr Gly Glu Pro Arg Tyr Val Asp Asp
50                  55                  60

Phe Lys Gly Arg Phe Ala Phe Ser Leu Glu Thr Ser Ala Ser Thr Ala
65                  70                  75                  80

Tyr Leu Gln Ile Ile Asn Leu Lys Asn Glu Asp Thr Ala Thr Tyr Phe
                85                  90                  95

Cys Ala Arg Trp Asp His Gly His Gly Gly Phe Thr Tyr Trp Gly Gln
            100                 105                 110

Gly Thr Leu Val Thr Val Ser Ala Gly Gly Gly Gly Ser Gly Gly Gly
        115                 120                 125

Gly Ser Gly Gly Gly Gly Ser Asp Ile Val Leu Thr Gln Thr Thr Ala
    130                 135                 140

Ser Leu Ala Val Ser Leu Gly Gln Arg Ala Thr Met Ser Cys Arg Ala
145                 150                 155                 160

Thr Glu Ser Val Asp Ser Tyr Gly Lys Ser Phe Met Tyr Trp Phe Gln
                165                 170                 175

Gln Arg Ala Gly Gln Pro Pro Lys Leu Leu Ile Tyr Leu Ala Ser Asn
            180                 185                 190

Leu Glu Ser Val Val Pro Pro Arg Phe Ser Gly Ser Gly Ser Arg Thr
        195                 200                 205

Asp Phe Ser Leu Thr Ile Asp Pro Val Glu Ala Asp Asp Ala Ala Thr
    210                 215                 220

Tyr Tyr Cys Gln Gln Asn Asn Glu Asp Pro Phe Thr Phe Gly Ser Gly
225                 230                 235                 240

Thr Lys Leu Glu Ile Lys
                245
```

<210> SEQ ID NO 2
<211> LENGTH: 744
<212> TYPE: DNA
<213> ORGANISM: Artificial Sequence
<220> FEATURE:
<223> OTHER INFORMATION: Nucleic acid encoding single chain antibody

<400> SEQUENCE: 2

```
atggaggtaa agctgcagga gtctggacct gagctgaaga agcctggaga gacagtcaaa      60
atctcctgca aggcctctgg ttataccttc acagactatt caatgcactg ggtgatgcag     120
tctccaggaa agggtttaaa gtggatgggc tggataaaca ctgagactgg tgagcctaga     180
```

```
tatgttgatg acttcaaggg gcggtttgcc ttctctttgg aaacctctgc cagcactgcc      240
tatttgcaga tcatcaatct caaaaatgag gacacggcta catatttctg cgctagatgg      300
gaccacggcc acgggggtt tacttactgg ggccaaggga ctctggtcac tgtctctgca       360
ggtggcggtg gctcgggcgg tggtgggtcg ggtggcggcg gatcggatat tgtgctgaca      420
caaactacag cttctttggc tgtgtctcta gggcagaggg ccaccatgtc ctgcagagcc      480
actgaaagtg ttgatagtta tggcaaaagt tttatgtact ggttccagca gagagcagga     540
cagccaccca aactcctcat ctaccttgca tccaacctag aatctgtggt ccctcccagg      600
ttcagtggca gtgggtctag gacagacttc tccctcacca ttgatcctgt ggaggctgat     660
gatgctgcaa cctattactg tcaacaaaat aatgaggatc cattcacgtt cggctcgggg      720
acaaagttgg aaataaaact cgag                                             744

<210> SEQ ID NO 3
<211> LENGTH: 15
<212> TYPE: PRT
<213> ORGANISM: Artificial Sequence
<220> FEATURE:
<223> OTHER INFORMATION: Linker

<400> SEQUENCE: 3

Gly Gly Gly Gly Ser Gly Gly Gly Gly Ser Gly Gly Gly Gly Ser
 1               5                  10                  15

<210> SEQ ID NO 4
<211> LENGTH: 5819
<212> TYPE: DNA
<213> ORGANISM: Artificial Sequence
<220> FEATURE:
<223> OTHER INFORMATION: Vector pc12A10scFv 3X HA

<400> SEQUENCE: 4
gacggatcgg gagatctccc gatccctat ggtgcactct cagtacaatc tgctctgatg        60
ccgcatagtt aagccagtat ctgctccctg cttgtgtgtt ggaggtcgct gagtagtgcg      120
cgagcaaaat ttaagctaca acaaggcaag gcttgaccga caattgcatg aagaatctgc      180
ttagggttag gcgttttgcg ctgcttcgcg atgtacgggc cagatatacg cgttgacatt      240
gattattgac tagttattaa tagtaatcaa ttacggggtc attagttcat agcccatata      300
tggagttccg cgttacataa cttacggtaa atggcccgcc tggctgaccg cccaacgacc      360
cccgcccatt gacgtcaata atgacgtatg ttcccatagt aacgccaata gggactttcc      420
attgacgtca atgggtggag tatttacggt aaactgccca cttggcagta catcaagtgt      480
atcatatgcc aagtacgccc cctattgacg tcaatgacgg taaatggccc gcctggcatt      540
atgcccagta catgacctta tgggactttc ctacttggca gtacatctac gtattagtca      600
tcgctattac catggtgatg cggttttggc agtacatcaa tgggcgtgga tagcggtttg      660
actcacgggg atttccaagt ctccacccca ttgacgtcaa tgggagtttg ttttggcacc      720
aaaatcaacg ggactttcca aaatgtcgta caactccgc cccattgacg caaatgggcg       780
gtaggcgtgt acggtgggag gtctatataa gcagagctct ctggctaact agagaaccca      840
ctgcttactg gcttatcgaa attaatacga ctcactatag ggagacccaa gctggctagt      900
taagcttacc atggaggtaa agctgcagga gtctggacct gagctgaaga gcctggaga      960 gacagtcaag atctcctgca aggcctctgg ttataccttc acagactatt caatgcactg     1020
ggtgatgcag tctccaggaa agggtttaaa gtggatgggc tggataaaca ctgagactgg    1080
```

```
tgagcctaga tatgttgatg acttcaaggg gcggtttgcc ttctctttgg aaacctctgc    1140
cagcactgcc tatttgcaga tcatcaatct caaaaatgag gacacggcta catatttctg    1200
cgctagatgg gaccacggcc acgggggtt  tacttactgg ggccaaggga ctctggtcac    1260
tgtctctgca gccggtggcg gtggctcggg cggtggtggg tcgggtggcg gcggatcgga    1320
tattgtgctg acacaaacta cagcttcttt ggctgtgtct ctagggcaga gggccaccat    1380
gtcctgcaga gccactgaaa gtgttgatag ttatggcaaa agttttatgt actggttcca    1440
gcagagagca ggacagccac ccaaactcct catctacctt gcatccaacc tagaatctgt    1500
ggtccctccc aggttcagtg gcagtgggtc taggacagac ttctccctca ccattgatcc    1560
tgtggaggct gatgatgctg caacctatta ctgtcaacaa ataatgagg  atccattcac    1620 gttcggctcg gggacaaagt tggaaataaa actcgaggga tcttacccat acgatgttcc    1680
tgactatgcg ggctatccct atgacgtccc ggactatgca ggatcctatc catatgacgt    1740
tccagattac gcttaggata aacccgctga tcagcctcga ctgtgccttc tagttgccag    1800
ccatctgttg tttgccccctc cccgtgcct  tccttgaccc tggaaggtgc cactcccact    1860
gtcctttcct aataaaatga ggaaattgca tcgcattgtc tgagtaggtg tcattctatt    1920 ctgggggtg  gggtggggca ggacagcaag ggggaggatt gggaagacaa tagcaggcat    1980 gctgggatg  cggtgggctc tatggcttct gaggcgaaa  gaaccagctg gggctctagg    2040
gggtatcccc acgcgccctg tagcggcgca ttaagcgcgg cgggtgtggt ggttacgcgc    2100
agcgtgaccg ctacacttgc cagcgcccta gcgcccgctc ctttcgcttt cttcccttcc    2160
tttctcgcca cgttcgccgg ctttccccgt caagctctaa atcgggggct ccctttaggg    2220
ttccgattta gtgctttacg gcacctcgac cccaaaaaac ttgattaggg tgatggttca    2280
cgtagtgggc catcgccctg atagacggtt tttcgccctt tgacgttgga gtccacgttc    2340
tttaatagtg gactcttgtt ccaaactgga acaacactca accctatctc ggtctattct    2400
tttgatttat aagggatttt gccgatttcg gcctattggt taaaaaatga gctgatttaa    2460
caaaaattta acgcgaatta attctgtgga atgtgtgtca gttagggtgt ggaaagtccc    2520
caggctcccc agcaggcaga agtatgcaaa gcatgcatct caattagtca gcaaccaggt    2580
gtggaaagtc cccaggctcc ccagcaggca gaagtatgca aagcatgcat ctcaattagt    2640
cagcaaccat agtcccgccc ctaactccgc ccatcccgcc cctaactccg cccagttccg    2700
cccattctcc gccccatggc tgactaattt tttttattta tgcagaggcc gaggccgcct    2760
ctgcctctga gctattccag aagtagtgag gaggcttttt tggaggccta ggcttttgca    2820
aaaagctccc gggagcttgt atatccattt tcggatctga tcagcacgtg ttgacaatta    2880
atcatcggca tagtatatcg gcatagtata atacgacaag gtgaggaact aaaccatggc    2940
caagcctttg tctcaagaag aatccaccct cattgaaaga gcaacggcta caatcaacag    3000
catccccatc tctgaagact acagcgtcgc cagcgcagct ctctctagcg acggccgcat    3060
cttcactggt gtcaatgtat atcatttttac tgggggacct tgtgcagaac tcgtggtgct    3120
gggcactgct gctgctgcgg cagctggcaa cctgacttgt atcgtcgcga tcggaaatga    3180
gaacaggggc atcttgagcc cctgcggacg gtgccgacag gtgcttctcg atctgcatcc    3240
tgggatcaaa gccatagtga aggacagtga tggacagccg acggcagttg ggattcgtga    3300
attgctgccc tctggttatg tgtgggaggg ctaagcactt cgtggccgag gagcaggact    3360
gacacgtgct acgagatttc gattccaccg ccgccttcta tgaaaggttg gcttcggaa    3420 tcgttttccg ggacgccggc tggatgatcc tccagcgcgg ggatctcatg ctggagttct    3480
```

```
tcgcccaccc caacttgttt attgcagctt ataatggtta caaataaagc aatagcatca   3540
caaatttcac aaataaagca ttttttttcac tgcattctag ttgtggtttg tccaaactca   3600
tcaatgtatc ttatcatgtc tgtataccgt cgacctctag ctagagcttg gcgtaatcat   3660
ggtcatagct gtttcctgtg tgaaattgtt atccgctcac aattccacac aacatacgag   3720
ccggaagcat aaagtgtaaa gcctggggtg cctaatgagt gagctaactc acattaattg   3780
cgttgcgctc actgcccgct ttccagtcgg gaaacctgtc gtgccagctg cattaatgaa   3840
tcggccaacg cgcggggaga ggcggtttgc gtattgggcg ctcttccgct tcctcgctca   3900
ctgactcgct gcgctcggtc gttcggctgc ggcgagcgg  atcagctcac tcaaaggcgg   3960
taatacggtt atccacagaa tcaggggata acgcaggaaa gaacatgtga gcaaaaggcc   4020
agcaaaaggc caggaaccgt aaaaaggccg cgttgctggc gttttccat aggctccgcc    4080 cccctgacga gcatcacaaa aatcgacgct caagtcagag gtggcgaaac ccgacaggac   4140
tataaagata ccaggcgttt ccccctggaa gctccctcgt gcgctctcct gttccgaccc   4200
tgccgcttac cggatacctg tccgcctttc tcccttcggg aagcgtggcg ctttctcata   4260
gctcacgctg taggtatctc agttcggtgt aggtcgttcg ctccaagctg ggctgtgtgc   4320
acgaaccccc cgttcagccc gaccgctgcg ccttatccgg taactatcgt cttgagtcca   4380
acccggtaag acacgactta tcgccactgg cagcagccac tggtaacagg attagcagag   4440
cgaggtatgt aggcggtgct acagagttct tgaagtggtg gcctaactac ggctacacta   4500
gaagaacagt atttggtatc tgcgctctgc tgaagccagt taccttcgga aaaagagttg   4560
gtagctcttg atccggcaaa caaaccaccg ctggtagcgg tggttttttt gtttgcaagc   4620
agcagattac gcgcagaaaa aaaggatctc aagaagatcc tttgatcttt tctacggggt   4680
ctgacgctca gtggaacgaa aactcacgtt aagggatttt ggtcatgaga ttatcaaaaa   4740
ggatcttcac ctagatcctt ttaaattaaa aatgaagttt taaatcaatc taagtatat    4800 atgagtaaac ttggtctgac agttaccaat gcttaatcag tgaggcacct atctcagcga   4860
tctgtctatt tcgttcatcc atagttgcct gactccccgt cgtgtagata actacgatac   4920
gggagggctt accatctggc cccagtgctg caatgatacc gcgagaccca cgctcaccgg   4980
ctccagattt atcagcaata aaccagccag ccggaagggc cgagcgcaga agtggtcctg   5040
caactttatc cgcctccatc cagtctatta attgttgccg ggaagctaga gtaagtagtt   5100
cgccagttaa tagtttgcgc aacgttgttg ccattgctac aggcatcgtg gtgtcacgct   5160
cgtcgtttgg tatggcttca ttcagctccg gttcccaacg atcaaggcga gttacatgat   5220
cccccatgtt gtgcaaaaaa gcggttagct ccttcggtcc tccgatcgtt gtcagaagta   5280
agttggccgc agtgttatca ctcatggtta tggcagcact gcataattct cttactgtca   5340
tgccatccgt aagatgcttt tctgtgactg gtgagtactc aaccaagtca ttctgagaat   5400
agtgtatgcg gcgaccgagt tgctcttgcc cggcgtcaat acgggataat accgcgccac   5460
atagcagaac tttaaaagtg ctcatcattg gaaaacgttc ttcggggcga aaactctcaa   5520
ggatcttacc gctgttgaga tccagttcga tgtaacccac tcgtgcaccc aactgatctt   5580
cagcatcttt tactttcacc agcgtttctg ggtgagcaaa aacaggaagg caaaatgccg   5640
caaaaaaggg aataagggcg acacggaaat gttgaatact catactcttc ctttttcaat   5700
attattgaag catttatcag ggttattgtc tcatgagcgg atacatattt gaatgtattt   5760
agaaaaataa acaaataggg gttccgcgca catttccccg aaaagtgcca cctgacgtc    5819
```

<210> SEQ ID NO 5

```
<211> LENGTH: 37
<212> TYPE: PRT
<213> ORGANISM: Artificial Sequence
<220> FEATURE:
<223> OTHER INFORMATION: 3X HA epitope

<400> SEQUENCE: 5

Gly Ser Tyr Pro Tyr Asp Val Pro Asp Tyr Ala Gly Tyr Pro Tyr Asp
  1               5                  10                  15

Val Pro Asp Tyr Ala Gly Ser Tyr Pro Tyr Asp Val Pro Asp Tyr Ala
             20                  25                  30

Ala Gln Cys Gly Arg
            35
```

US 8,552,155 B2

ANTI-PYK2 ANTIBODIES

CROSS-REFERENCE TO RELATED APPLICATIONS

This application is a National Stage application under 35 U.S.C. 371 and claims benefit under 35 U.S.C. 119(a) of International Application No. PCT/US2009/045495, having an International Filing Date of May 28, 2009, which claims benefit of priority from U.S. Provisional Application Ser. No. 61/056,727, filed on May 28, 2008. The disclosures of the prior applications are considered part of (and are incorporated by reference in) the disclosure of this application.

TECHNICAL FIELD

This document provides methods and materials related to anti-Pyk2 antibodies.

BACKGROUND

Pyk2 is a ~116 kDa non-receptor tyrosine kinase polypeptide that shares a conserved domain structure with FAK (Sasaki et al., *J. Biol. Chem.*, 270(36):21206-19 (1995) and Avraham et al., *J. Biol. Chem.*, 270(46):27742-51 (1995)). Both FAK and Pyk2 polypeptides contain a N-terminal divergent FERM domain, a central kinase domain, a C-terminal domain with two proline-rich regions that dock numerous adapter and effector molecules (Andreev et al., *Mol. Cell. Biol.*, 19(3):2338-50 (1999); Ren et al., *J. Cell Biol.*, 152(5): 971-84 (2001); and Kruljac-Letunic et al., *J. Biol. Chem.*, 278(32):29560-70 (2003)) and share some, but not all, phosphorylation sites. Pyk2 polypeptides have a more limited normal tissue distribution being most highly expressed in brain, osteoclasts, and cells of hematologic lineage (Sasaki et al., *J. Biol. Chem.*, 270(36):21206-19 (1995) and Avraham et al., *J. Biol. Chem.*, 270(46):27742-51 (1995)). Pyk2 polypeptides have also been implicated in the invasive pathobiology of several cancers (Gutenberg et al., *Acta Neuropathol.* (Berl), 108(3):224-30 (2004); Zrihan-Licht et al., *Int. J. Oncol.*, 24(1):153-9 (2004); and Hoelzinger et al., *Neoplasia*, 7(1):7-16 (2005)). Pyk2 polypeptides are activated by a diverse set of upstream signals most notably elevation of intracellular calcium but also by G-protein coupled receptors, growth factor receptors, and integrin mediated adhesion (Avraham et al., *Cell Signal*, 12(3):123-33 (2000)).

SUMMARY

This document provides methods and materials related to anti-Pyk2 antibodies. For example, this document provides anti-Pyk2 antibodies, methods for making anti-Pyk2 antibodies, and methods for using an anti-Pyk2 antibody to inhibit glioma cell migration, Pyk2 tyrosine phosphorylation, or effector coupling to the N-terminal FERM domain independent of Pyk2 activation.

In general, one aspect of this document features a substantially pure antibody having binding affinity for an F3 subdomain of a Pyk2 polypeptide. The Pyk2 polypeptide can be a human Pyk2 polypeptide. The F3 subdomain can be amino acid residues 263 to 357 of a human Pyk2 polypeptide. The antibody can have less than $10^4$ mol$^{-1}$ binding affinity for a tyrosine kinase FAK polypeptide. The antibody can be a monoclonal antibody. The antibody can be a single chain antibody. The antibody can have the amino acid sequence set forth in SEQ ID NO:1. The antibody can have the binding characteristics of an antibody having the amino acid sequence set forth in SEQ ID NO:1.

In another aspect, this document features a method for inhibiting glioma cell migration. The method comprises, or consists essentially of, administering an antibody to a glioma cell, wherein the antibody comprises a binding affinity for an F3 subdomain of a Pyk2 polypeptide. The Pyk2 polypeptide can be a human Pyk2 polypeptide. The F3 subdomain can be amino acid residues 263 to 357 of a human Pyk2 polypeptide. The antibody can have less than $10^8$ mol$^{-1}$ binding affinity (e.g., less than $10^7$, $10^6$, $10^5$, or $10^4$ mol$^{-1}$ binding affinity) for a tyrosine kinase FAK polypeptide. The antibody can be a monoclonal antibody. The antibody can be a single chain antibody. The antibody can have the amino acid sequence set forth in SEQ ID NO:1. The antibody can have the binding characteristics of an antibody having the amino acid sequence set forth in SEQ ID NO:1. The administering step can include administering a viral vector containing a nucleic acid sequence that encodes the antibody. The viral vector can be a lentiviral vector.

In another aspect, this document features a method for inhibiting Pyk2 tyrosine phosphorylation. The method comprises, or consists essentially of, administering an antibody to a cell, wherein the antibody comprises a binding affinity for an F3 subdomain of a Pyk2 polypeptide. The Pyk2 polypeptide can be a human Pyk2 polypeptide. The F3 subdomain can be amino acid residues 263 to 357 of a human Pyk2 polypeptide. The antibody can have less than $10^4$ mol$^{-1}$ binding affinity for a tyrosine kinase FAK polypeptide. The antibody can be a monoclonal antibody. The antibody can be a single chain antibody. The antibody can have the amino acid sequence set forth in SEQ ID NO:1. The antibody can have the binding characteristics of an antibody having the amino acid sequence set forth in SEQ ID NO:1. The administering step can include administering a viral vector containing a nucleic acid sequence that encodes the antibody. The viral vector can be a lentiviral vector.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 2 (top) is a three dimensional model of the Pyk2 FERM with the locations of interacting residues, indicated by Arial font and non-interacting surfaces indicated by Times Roman font.

FIG. 3 contains the nucleic acid sequence (SEQ ID NO:2) that encoding the amino acid sequence (SEQ ID NO:1) of a 12A10 single chain antibody. VH=variable heavy; VL=variable light. The underlined sequence (SEQ ID NO:3) represents a linker sequence. The bold residues indicate the complementarity determining regions (CDRs).

FIG. 8 contains the graphical representation of a pc12A10scFv 3× HA vector together with its nucleic acid sequence (SEQ ID NO:4).

FIG. 9 contains the translated amino acid sequence (SEQ ID NO:1) for 12A10scFv with a C-terminal 3× HA epitope (GSYPYDVPDYAGYPYDVPD-YAGSYPYDVP-DYAAQCGR; SEQ ID NO:5). The sequence contains an LE amino acid sequence between that of SEQ ID NO:1 and the C-terminal 3× HA epitope.

DETAILED DESCRIPTION

Figure 1:
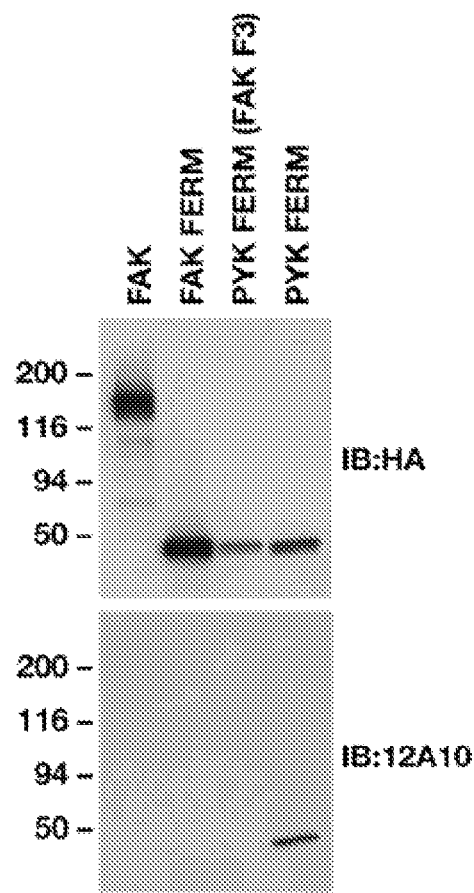
FIG. 1 is a photograph of a Western blot using a rabbit monoclonal anti-HA epitope antibody (top panel) and murine monoclonal antibody 12A10 (bottom panel) to probe lysates obtained from SF767 cells expressing the indicated polypeptides.

This document provides methods and materials related to anti-Pyk2 antibodies. For example, this document provides anti-Pyk2 antibodies, methods for making anti-Pyk2 antibodies, and methods for using an anti-Pyk2 antibody to inhibit glioma cell migration or functionally important protein-protein interactions. In some cases, the antibodies provided herein can bind to an F3 subdomain of a Pyk2 polypeptide with little or no detectable binding to a tyrosine kinase FAK polypeptide. For example, an antibody provided herein can bind to an F3 subdomain of a human Pyk2 polypeptide without binding to a human tyrosine kinase FAK polypeptide. An example of an antibody having the ability to bind to an F3 subdomain of a Pyk2 polypeptide with little or no detectable binding to a tyrosine kinase FAK polypeptide includes, without limitation, an anti-Pyk2 12A10 single chain antibody (scFv) having the amino acid sequence set forth in SEQ ID NO:1.

The term "antibody" as used herein refers to intact antibodies as well as antibody fragments that retain some ability to bind an epitope. Such fragments include, without limitation, Fab, F(ab')2, and Fv antibody fragments. The term "epitope" refers to an antigenic determinant on an antigen to which the paratope of an antibody binds. Epitopic determinants usually consist of chemically active surface groupings of molecules (e.g., amino acid or sugar residues) and usually have specific three dimensional structural characteristics as well as specific charge characteristics.

The antibodies provided herein can be any antibody (e.g., a monoclonal antibody) having specific binding affinity for a Pyk2 polypeptide (e.g., an F3 subdomain of a Pyk2 polypeptide) with little or no detectable binding to a tyrosine kinase FAK polypeptide. Such antibodies can be used in immunoassays in liquid phase or bound to a solid phase. For example, the antibodies provided herein can be used in competitive and non competitive immunoassays in either a direct or indirect format. Examples of such immunoassays include the radioimmunoassay (RIA) and the sandwich (immunometric) assay. In some cases, the antibodies provided herein can be used to inhibit glioma cell migration.

Antibodies provided herein can be prepared using any method. For example, any substantially pure Pyk2 polypeptide, or fragment thereof, can be used as an immunogen to elicit an immune response in an animal such that specific antibodies are produced. Thus, an intact full-length Pyk2 polypeptide or fragments containing small polypeptides can be used as an immunizing antigen. In addition, the immunogen used to immunize an animal can be chemically synthesized or derived from translated cDNA. Further, the immunogen can be conjugated to a carrier polypeptide, if desired. Commonly used carriers that are chemically coupled to an immunizing polypeptide include, without limitation, keyhole limpet hemocyanin (KLH), thyroglobulin, bovine serum albumin (BSA), and tetanus toxoid.

The preparation of polyclonal antibodies is well-known to those skilled in the art. See, e.g., Green et al., Production of Polyclonal Antisera, in IMMUNOCHEMICAL PROTOCOLS (Manson, ed.), pages 1 5 (Humana Press 1992) and Coligan et al., Production of Polyclonal Antisera in Rabbits, Rats, Mice and Hamsters, in CURRENT PROTOCOLS IN IMMUNOLOGY, section 2.4.1 (1992). In addition, those of skill in the art will know of various techniques common in the immunology arts for purification and concentration of polyclonal antibodies, as well as monoclonal antibodies (Coligan, et al., Unit 9, Current Protocols in Immunology, Wiley Interscience, 1994).

The preparation of monoclonal antibodies also is well-known to those skilled in the art. See, e.g., Kohler & Milstein, *Nature* 256:495 (1975); Coligan et al., sections 2.5.1 2.6.7; and Harlow et al., ANTIBODIES: A LABORATORY MANUAL, page 726 (Cold Spring Harbor Pub. 1988). Briefly, monoclonal antibodies can be obtained by injecting mice with a composition comprising an antigen, verifying the presence of antibody production by analyzing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well established techniques. Such isolation techniques include affinity chromatography with Protein A Sepharose, size exclusion chromatography, and ion exchange chromatography. See, e.g., Coligan et al., sections 2.7.1 2.7.12 and sections 2.9.1 2.9.3; Barnes et al., Purification of Immunoglobulin G (IgG), in METHODS 1N MOLECULAR BIOLOGY, VOL. 10, pages 79 104 (Humana Press 1992).

In addition, methods of in vitro and in vivo multiplication of monoclonal antibodies is well known to those skilled in the art. Multiplication in vitro can be carried out in suitable culture media such as Dulbecco's Modified Eagle Medium or RPMI 1640 medium, optionally replenished by mammalian serum such as fetal calf serum, or trace elements and growth sustaining supplements such as normal mouse peritoneal exudate cells, spleen cells, and bone marrow macrophages. Production in vitro provides relatively pure antibody preparations and allows scale up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells (e.g., osyngeneic mice) to cause growth of antibody producing tumors. Optionally, the animals are primed with a hydrocarbon, especially oils such as pristane (tetramethylpentadecane) prior to injection. After one to three weeks, the desired monoclonal antibody is recovered from the body fluid of the animal.

In some cases, the antibodies provided herein can be made using non-human primates. General techniques for raising therapeutically useful antibodies in baboons can be found, for example, in Goldenberg et al., International Patent Publication WO 91/11465 (1991) and Losman et al., *Int. J. Cancer,* 46:310 (1990).

In some cases, the antibodies can be humanized monoclonal antibodies. Humanized monoclonal antibodies can be produced by transferring mouse complementarity determining regions (CDRs) from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions when treating humans. General techniques for cloning murine immunoglobulin variable domains are described, for example, by Orlandi et al., *Proc. Nat'l. Acad. Sci. USA* 86:3833 (1989). Techniques for producing humanized monoclonal antibodies are described, for example, by Jones et al., *Nature* 321:522 (1986); Riechmann et al., *Nature* 332:323 (1988); Verhoeyen et al., *Science* 239:1534 (1988); Carter et al., *Proc. Nat'l. Acad. Sci. USA* 89:4285 (1992); Sandhu, *Crit. Rev. Biotech.* 12:437 (1992); and Singer et al., *J. Immunol.* 150:2844 (1993).

Antibodies provided herein can be derived from human antibody fragments isolated from a combinatorial immunoglobulin library. See, for example, Barbas et al., METHODS: A COMPANION TO METHODS IN ENZYMOLOGY, VOL. 2, page 119 (1991) and Winter et al., *Ann. Rev. Immunol.* 12: 433 (1994). Cloning and expression vectors that are useful for producing a human immunoglobulin phage library can be obtained, for example, from STRATAGENE Cloning Systems (La Jolla, Calif.).

In addition, antibodies provided herein can be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens and can be used to produce human antibody secreting hybridomas. Methods for obtaining human antibodies from transgenic mice are described by Green et al., *Nature Genet.* 7:13 (1994); Lonberg et al., *Nature* 368:856 (1994); and Taylor et al., *Int. Immunol.* 6:579 (1994).

Antibody fragments can be prepared by proteolytic hydrolysis of an intact antibody or by the expression of a nucleic acid encoding the fragment. Antibody fragments can be obtained by pepsin or papain digestion of intact antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. In some cases, an enzymatic cleavage using pepsin can be used to produce two monovalent Fab' fragments and an Fc fragment directly. These methods are described, for example, by Goldenberg (U.S. Pat. Nos. 4,036,945 and 4,331,647). See also Nisonhoff et al., *Arch. Biochem. Biophys.* 89:230 (1960); Porter, *Biochem. J.* 73:119 (1959); Edelman et al., METHODS IN ENZYMOLOGY, VOL. 1, page 422 (Academic Press 1967); and Coligan et al. at sections 2.8.1 2.8.10 and 2.10.1 2.10.4.

Other methods of cleaving antibodies, such as separation of heavy chains to form monovalent light heavy chain fragments, further cleavage of fragments, or other enzymatic, chemical, or genetic techniques may also be used provided the fragments retain some ability to bind (e.g., selectively bind) its epitope.

The antibodies provided herein can be substantially pure. The term "substantially pure" as used herein with reference to an antibody means the antibody is substantially free of other polypeptides, lipids, carbohydrates, and nucleic acid with which it is naturally associated. Thus, a substantially pure antibody is any antibody that is removed from its natural environment and is at least 60 percent pure. A substantially pure antibody can be at least about 65, 70, 75, 80, 85, 90, 95, or 99 percent pure.

A nucleic acid encoding an antibody provided herein (e.g., a 12A10 scFv antibody) can be administered to a mammal using any appropriate method. For example, a nucleic acid can be administered to a mammal using a vector such as a viral vector.

Vectors for administering nucleic acids (e.g., a nucleic acid encoding a scFv antibody provided herein) to a mammal are known in the art and can be prepared using standard materials (e.g., packaging cell lines, helper viruses, and vector constructs). See, for example, *Gene Therapy Protocols* (*Methods* in *Molecular Medicine*), edited by Jeffrey R. Morgan, Humana Press, Totowa, N.J. (2002) and *Viral Vectors for Gene Therapy: Methods and Protocols*, edited by Curtis A. Machida, Humana Press, Totowa, N. J. (2003). Virus-based nucleic acid delivery vectors are typically derived from animal viruses, such as adenoviruses, adeno-associated viruses, retroviruses, lentiviruses, vaccinia viruses, herpes viruses, and papilloma viruses.

Lentiviruses are a genus of retroviruses that can be used to infect neuronal cells and non-dividing cells. Adenoviruses contain a linear double-stranded DNA genome that can be engineered to inactivate the ability of the virus to replicate in the normal lytic life cycle. Adenoviruses can be used to infect dividing and non-dividing cells. Adenoviral vectors can be introduced and efficiently expressed in cerebrospinal fluid and in brain. Adeno-associated viruses also can be used to infect non-dividing cells. Muscle cells and neurons can be efficient targets for nucleic acid delivery by adeno-associated viruses. Additional examples of viruses that can be used as viral vectors include herpes simplex virus type 1 (HSV-1). HSV-1 can be used as a neuronal gene delivery vector to establish a lifelong latent infection in neurons. HSV-1 can package large amounts of foreign DNA (up to about 30-40 kb). The HSV latency-associated promoter can be used to allow high levels of expression of nucleic acids during periods of viral latency.

Vectors for nucleic acid delivery can be genetically modified such that the pathogenicity of the virus is altered or removed. The genome of a virus can be modified to increase infectivity and/or to accommodate packaging of a nucleic acid, such as a nucleic acid encoding a 12A10 scFv antibody. A viral vector can be replication-competent or replication-defective, and can contain fewer viral genes than a corresponding wild-type virus or no viral genes at all.

In addition to nucleic acid encoding an antibody provided herein, a viral vector can contain regulatory elements operably linked to a nucleic acid encoding an antibody provided herein. Such regulatory elements can include promoter sequences, enhancer sequences, response elements, signal peptides, internal ribosome entry sequences, polyadenylation signals, terminators, or inducible elements that modulate expression (e.g., transcription or translation) of a nucleic acid. The choice of element(s) that may be included in a viral vector depends on several factors, including, without limitation, inducibility, targeting, and the level of expression desired. For example, a promoter can be included in a viral vector to facilitate transcription of a nucleic acid encoding an antibody provided herein. A promoter can be constitutive or inducible (e.g., in the presence of tetracycline), and can affect the expression of a nucleic acid encoding an antibody provided herein in a general or tissue-specific manner. Tissue-specific promoters include, without limitation, enolase promoter, prion protein (PrP) promoter, and tyrosine hydroxylase promoter.

As used herein, "operably linked" refers to positioning of a regulatory element in a vector relative to a nucleic acid in such a way as to permit or facilitate expression of the encoded antibody. For example, a viral vector can contain a neuronal-specific enolase promoter and a nucleic acid encoding an antibody provided herein. In this case, the enolase promoter is operably linked to a nucleic acid encoding an antibody provided herein such that it drives transcription in neuronal tissues.

The invention will be further described in the following examples, which do not limit the scope of the invention described in the claims.

EXAMPLES

Example 1

Anti-Pyk2 Antibodies

Antibodies. The anti-FLAG M2 monoclonal antibody was obtained from Sigma (St. Louis, Mo.). The rabbit anti-HA monoclonal antibody was obtained from Upstate Biotechnology (Lake Placid, N.Y.). The anti-phospho tyrosine pY20 monoclonal antibody was obtained from BD Biosciences (San Diego, Calif.). The anti-Pyk2 monoclonal antibody OT126 was obtained from United States Biologicals (Swampscott, Mass.). The HRP-conjugated Fcγ fragment specific goat anti-mouse IgG was obtained from Jackson ImmunoResearch Laboratories (West Grove, Pa.).

Cell Culture. The human glioblastoma cell line SF767 and the 293T packaging cells were routinely passaged in DMEM containing 10% fetal bovine serum, 1% nonessential amino acids, 2 mM glutamine, 100 units/mL penicillin, and 10 μg/mL streptomycin.

Expression constructs. The construction of the FLAG-epitope tagged wild type Pyk2 and the HA-epitope tagged Pyk2 FERM domain is described elsewhere (Lipinski et al., *Neoplasia*, 7:435-445 (2005)). The HA-epitope tagged wild type FAK is described elsewhere ((Lipinski et al., *Mol. Cancer. Res.*, 1:323-332 (2003)). Pyk2 containing select amino acid substitutions (W104A, Y135C, I308E, D346A, D350A) and the Pyk2 FERM I308E variant are described elsewhere (Lipinski et al., *Biochem. Biophys. Res. Commun.*, 349:939-947 (2006)). Additional Pyk2 amino acid substitutions (R306E, I348E, Y351A and R353A) were introduced into FLAG tagged Pyk2 using the Quickchange site-directed mutagenesis kit (Stratagene, La Jolla, Calif.). The FAK FERM domain, encoding FAK residues R35-P362, was amplified by PCR and cloned in-frame downstream of a 3× HA epitope in pcDNA3. In the Pyk2 FERM (FAKF3) construct, the Pyk2 FERM F3 module (residues D261-A366) was replaced by the corresponding FAK F3 module (residues D254-P362) by splice overlap extension PCR and cloned in-frame downstream of a 3× HA epitope in pcDNA3. The Pyk2 F3 module sequence encoding amino acid residues D261-A366 was cloned into the inducible expression vector pET28 (Novagen) downstream of a 6× His tag.

Generation of monoclonal antibody 12A10. The mouse monoclonal antibody 12A10 was generated against the F3 module of the Pyk2 FERM domain. The pET28 Pyk2 F3 construct was transformed into *E. coli* BL21. Bacterial suspensions were grown at 30° C. to mid-log phase ($OD_{600}$=0.5), and protein expression was induced by the addition of 0.1 M IPTG (isopropyl β-D-thiogalactopyranoside). Sixty minutes after induction, bacterial cells were pelleted and frozen at −80° C. Frozen pellets were thawed on ice in CelLytic B cell lysis reagent (Sigma) containing protease inhibitors. The lysates were clarified by centrifugation, and recombinant F3 was purified by FPLC on a Ni-NTA column.

Five Balb/C mice were each administered 40 μg of purified F3 in RIBI adjuvant (Sigma) via intraperitoneal injection followed by two booster administrations at days 14 and 28. The immunoreactivity of the sera following the second booster injection against the purified F3 immunogen was compared to the immunoreactivity of mouse pre-bleed sera by ELISA assay. Three mice with substantial anti-F3 serum titers were splenectomized, and the B-lymphocytes fused with the myeloma cell line P3X63-Ag8.653 (ATCC-1580) to generate hybridomas. Subcloning of hybridomas was done by limiting dilution. Hybridoma supernatants were screened for immunoreactivity with the full length Pyk2 FERM domain (residues R39-A366) by a capture sandwich ELISA. The wells of a microtiter plate were coated with 100 ng of rabbit monoclonal anti-HA epitope antibody followed by the addition of 100 µg of cell lysates from 293 cells transfected with HA-epitope tagged Pyk2 FERM. The wells were washed, and 100 µL of hybridoma supernatant was added to each well. The wells were washed and incubated with a 1:10,000 dilution of a HRP-conjugated Fcγ fragment specific goat anti-mouse IgG. The wells were then developed with 10 µM O-phenylene diamine and were read at 490 nM. Six hybridomas that exhibited significant immunoreactivity with the wild type Pyk2 FERM domain were subsequently screened against the Pyk2 FERM variant I308E as described elsewhere (Lipinski et al., Biochem. Biophys. Res. Commun., 349:939-947 (2006)). One hybridoma, designated 12A10, bound to the wild type Pyk2 FERM domain but failed to bind to Pyk2 FERM I308E. The 12A10 hybridoma was expanded, and IgG purified from culture media using Protein G Sepharose column chromatography. The 12A10 hybridoma was isotyped and found to be $IgG_1$.

Cloning of 12A10 $V_H$ and $V_L$ genes and scFv construction. To generate 12A10 scFv, total RNA from hybridoma 12A10 cells was isolated using the Trizol reagent (Biotex, Houston, Tex.). First strand cDNA was synthesized with the kit from BD Biosciences. The cDNAs for the $V_H$ and $V_L$ domains were amplified by PCR using Taq polymerase and degenerate primers as described elsewhere (Wang et al., J. Immunol. Methods, 233:167-177 (2000)). The PCR products for $V_H$ and $V_L$ were ligated into the pCR2.1 TA cloning vector (Invitrogen, San Diego, Calif.) and sequenced. The 12A10 scFv was generated by joining the $V_H$ and $V_L$ sequences together by splice overlap PCR using oligonucleotides primers that encoded a $(Gly_4Ser)_3$ linker between the C-terminus of the $V_H$ and the N-terminus of the $V_L$. The resulting PCR fragment was ligated upstream of either a myc or HA-epitope in expression vector pcDNA3 (Invitrogen) and designated pc12A10 scFv. The sequence for a vector containing a sequence encoding 12A10 scFv with an HA tag was designated pc12A10 scFv 3× HA and is set forth in FIG. 8. The amino acid sequence of 12A10 scFv 3× HA is set forth in FIG. 9. For stable transduction of glioma cell lines, a fragment containing the myc-epitope tagged 12A10 scFv was excised from pc12A10 scFv and ligated into the lentiviral plasmid vector pWPXL (Addgene, Cambridge, Mass.). The 12A10 scFv was expressed by the EF1-α promoter as part of a bicistronic unit encoding DsRed using the encephalomyocarditis virus 5' internal ribosome entry site as described elsewhere (Wiznerowicz & Trono, J. Virol., 77:8957-8961 (2003)).

Lentiviral transduction. Recombinant lentiviruses were produced by transient transfection of 293T cells with 20 µg of the appropriate lentiviral transfer vector construct, 15 µg of psPAX2 packaging plasmid, and 5 µg of pMD2G-VSVG envelope vector by calcium phosphate precipitation. Recombinant lentivirus containing supernatants were harvested 48 hours after transfection. For lentiviral transduction, medium containing recombinant 12A10 scFv lentiviruses was added to sub-confluent cultures of SF767 cells. Control SF767 cells were transduced with pWPXL expressing GFP. Forty-eight hours after infection, cells were harvested, and GFP or RFP positive cells were collected by mass sorting on a FACS Vantage flow cytometer (BD Biosciences, San Jose, Calif.).

Immunoblotting and immunoprecipitation. Cells were washed in cold PBS, lysed by addition of 1 mL IPB buffer: 137 mM NaCl, 20 mM Tris, pH 7.5, 1% NP-40, and 10% glycerol containing protease and phosphatase inhibitors and incubated on ice for 30 minutes. Lysates were clarified by centrifugation at 16,000×g for 10 minutes at 4° C. Protein content of the lysate was determined using the BCA assay (Sigma).

Immunoprecipitation of cleared lysates was performed as described elsewhere (Lipinski et al., Biochem. Biophys. Res. Commun., 349:939-947 (2006)). For immunoblotting, equal amounts of protein (10-20 µg) were electrophoresed on 8-16% gradient SDS-PAGE gels (Invitrogen, Carlsbad, Calif.) and transferred to nitrocellulose. Immunoblotting of transferred proteins was performed with the appropriate primary antibodies for 1 hour at room temperature and was visualized by enhanced chemiluminescence (Perkin Elmer Life Sciences, Boston, Mass.).

Generation of intracranial xenograft tumors. Female athymic nude mice (age 4-5 weeks) were randomized into groups of eight. Power analysis indicated that a sample size of eight animals for each group will have 80% power to detect a probability of 0.90 that the time until onset of a moribund state in one group is less than the time until onset of a moribund state in another group using a Wilcoxon (Mann-Whitney) rank sum test with a 0.05 two sided significance level. Each animal received either SF767 wild type control transduced cells or SF767 cells transduced with 12A10 scFv. Cells $(7.5×10^5)$ were delivered by intraparenchymal injection into the right cerebral hemisphere. Animals were first anesthetized with ketamine (10 mg/kg) and xylazine (90 mg/kg), and a 0.75 cm skin incision was made over the cranial midline. A burr hole was made through the skull 3 mm posterior and 3 mm lateral of bregma and afterwards, the mice were placed into the small animal stereotaxic frame. A micromanipulator bearing a 10 µL Hamilton syringe (30 gauge needle) was advanced through the burr hole until an intraparenchymal depth of 3 mm was reached. Tumor cells were delivered in 10 µL of PBS at a rate of 1 µL/min after which the needle was left an additional 10 minutes before removal. Following injection, the craniotomy was filled with bone wax, and the skin closed with 5-0 silk suture. Mice were weighed daily and observed for the onset of neurological symptoms or until moribund. When reaching the study end-point, animals were euthanized, and formalin-perfused brains were harvested for tissue analysis.

Radial Migration Assay. A monolayer radial migration assay was used as described elsewhere (Giese et al., Cancer Res., 54:3897-904 (1994)). Briefly, slides containing 10 individual 7-mm circular seeding areas surrounded by a hydrophobic template mask (Creative Scientific Methods Inc., Phoenix, Ariz.) were coated with 10 µg/mL laminin. Control or transduced cells were resuspended in DMEM containing 10% serum and seeded at a density of 2500 cells per well (internal diameter of 1 mm) of a Cell Sedimentation Manifold (Creative Scientific Methods Inc., Phoenix, Ariz.). After overnight incubation (16 hours), the manifold was removed, and an initial measurement ($t_0$) of the diameter of the cell colony was made using an inverted microscope (Axiovert; Carl Zeiss, Thornwood, N.Y.) and image analysis equipment (Scion Image, Frederick, Md.). The change in the diameter of the cell population over time was determined at 24 hours following the initial measurement. Slopes of the lines derived from the measurements (radius versus time) were used to calculate the migration rate of the cells. Linear migration from the initial seeded area at $t_0$ was determined for at least 10 replicate samples for each infected construct. Specific migration rates were calculated by normalizing the measurements to nonspecific migration on BSA. The absolute migration and migratory rates were calculated, and group means determined.

Results

Figure 2:
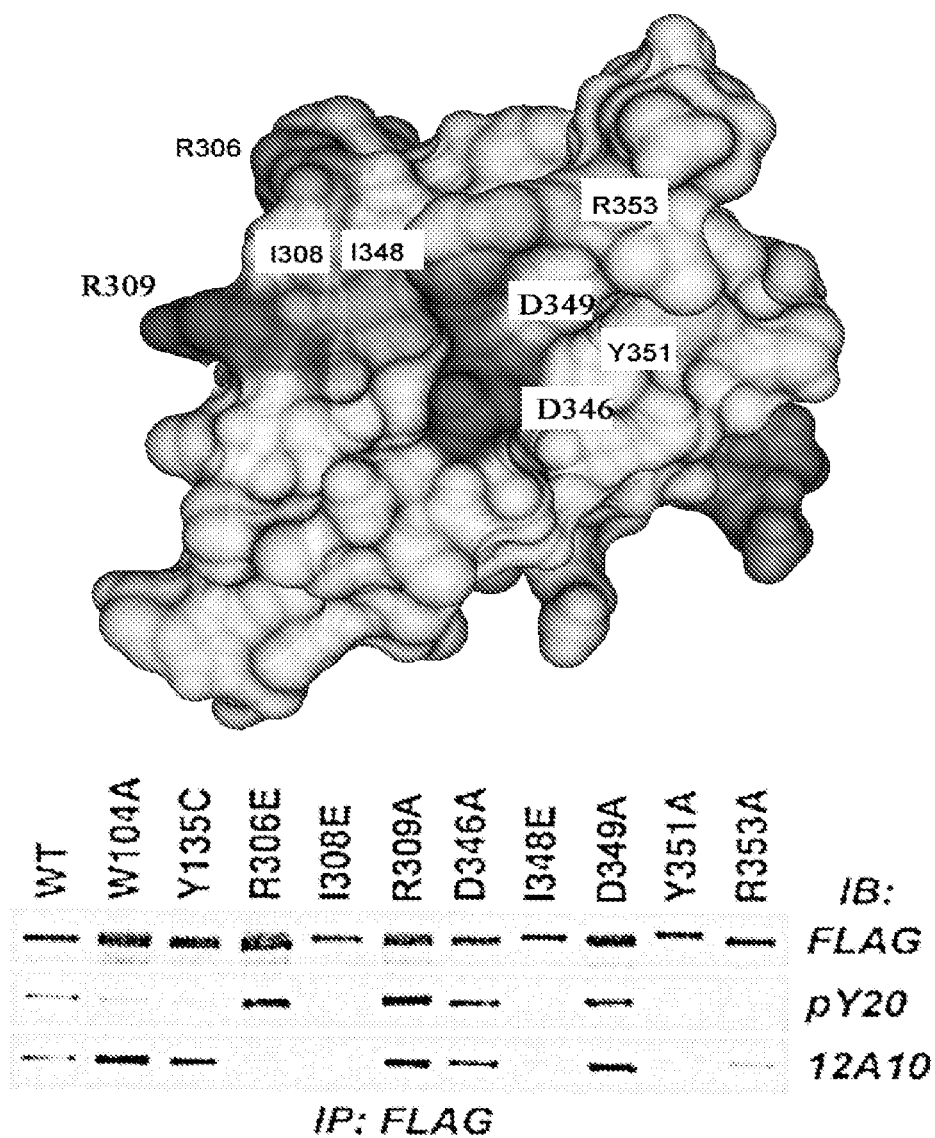
FIG. 2 (bottom panel) depicts a Western blot using anti-Pyk2 12A10 monoclonal antibody. SF767 cells were transfected with FLAG epitope tagged wild type (WT) Pyk2 or Pyk2 with the indicated amino acid substitution. Cells were lysed, Pyk2 was immunoprecipitated with anti-FLAG mAb, and immunoprecipitates immunoblotted with anti FLAG, anti-phosphotyrosine mAb pY20 or mAb 12A10.

The monoclonal antibody 12A10 binds to a functional site in the Pyk2 FERM domain. The Pyk2 FERM domain plays a role in the promigratory effect of Pyk2 in glioma cells (Lipinski et al., *Biochem. Biophys. Res. Commun.*, 349:939-947 (2006)). Notably, substitution of I308 in the F3 module of the Pyk2 FERM domain inhibited Pyk2 phosphorylation. In addition, substitution of I308 blocked the inhibitory activity of the autonomously expressed Pyk2 FERM domain. To further investigate the role of the Pyk2 FERM domain in regulating the pro-migratory activity of Pyk2, a monoclonal antibody targeting the F3 module of Pyk2 was generated. The monoclonal antibody, designated 12A10, reacted with the full length Pyk2 FERM domain but failed to react with full length FAK, the FAK FERM domain, or the Pyk2 FERM domain containing the FAK FERM F3 domain (FIG. 1). Several residues in the Pyk2 FERM F3 module were selected for site directed mutagenesis based on the 3D model of the Pyk2 FERM domain (Lipinski et al., *Biochem. Biophys. Res. Commun.*, 349:939-947 (2006)) and available ligand bound FERM domain crystal structures (Hamada et al., *EMBO J.*, 22:502-14 (2003), de Pereda et al., *J. Biol. Chem.*, (2004), and Garcia-Alvarez et al., *Mol. Cell.*, 11:49-58 (2003)), indicating the importance of a long shallow groove formed by residues from helix al and strand b5 on the surface of F3 in ligand binding. Cells transfected with FLAG-tagged Pyk2 or Pyk2 variants were lysed and immunoprecipitated with anti-FLAG antibodies. The effect of the substitutions on Pyk2 phosphorylation and 12A10 binding was examined by immunoblotting the immunoprecipitates with anti-phospho tyrosine antibody pY20 or antibody 12A10 (FIG. 2). None of the substitutions significantly inhibited Pyk2 expression, but the substitutions had variable effects on Pyk2 phosphorylation. As described elsewhere (Lipinski et al., *Biochem. Biophys. Res. Commun.*, 349:939-947 (2006)), substitution of I308 abrogated Pyk2 phosphorylation. Substitution of I308 also resulted in the loss of 12A10 binding. In addition, substitution of residues I348, Y351, and R353 also resulted in a loss of Pyk2 phosphorylation and either abolished or significantly reduced 12A10 binding. In contrast, substitution of residues R309, D346, or D350 did not inhibit Pyk2 phosphorylation or the binding of 12A10, whereas the substitution of R306 did not inhibit Pyk2 phosphorylation but blocked 12A10 binding. Substitution of residues W104 or Y135, which are located in the F1-F3 interface, inhibited Pyk2 phosphorylation but did not affect 12A10 binding. Together, these results demonstrate that the epitope of the 12A10 monoclonal antibody maps to the alpha1C-beta5C surface of the F3 module of the Pyk2 FERM domain.

Construction and characterization of 12A10 scFv. To generate the 12A10 scFv fragment, the cDNAs encoding the VH and VL sequences were reverse transcribed and amplified from mRNA from 12A10 hybridoma cells. Fragments encoding the $V_H$ and $V_L$ were joined by a $(G_4S)_3$ linker by splice overlap PCR and ligated upstream of a 3× HA epitope in expression vector pcDNA3. The nucleotide and deduced amino acid sequence of the 12A10 scFv is set forth in FIG. 3.

Figure 5:
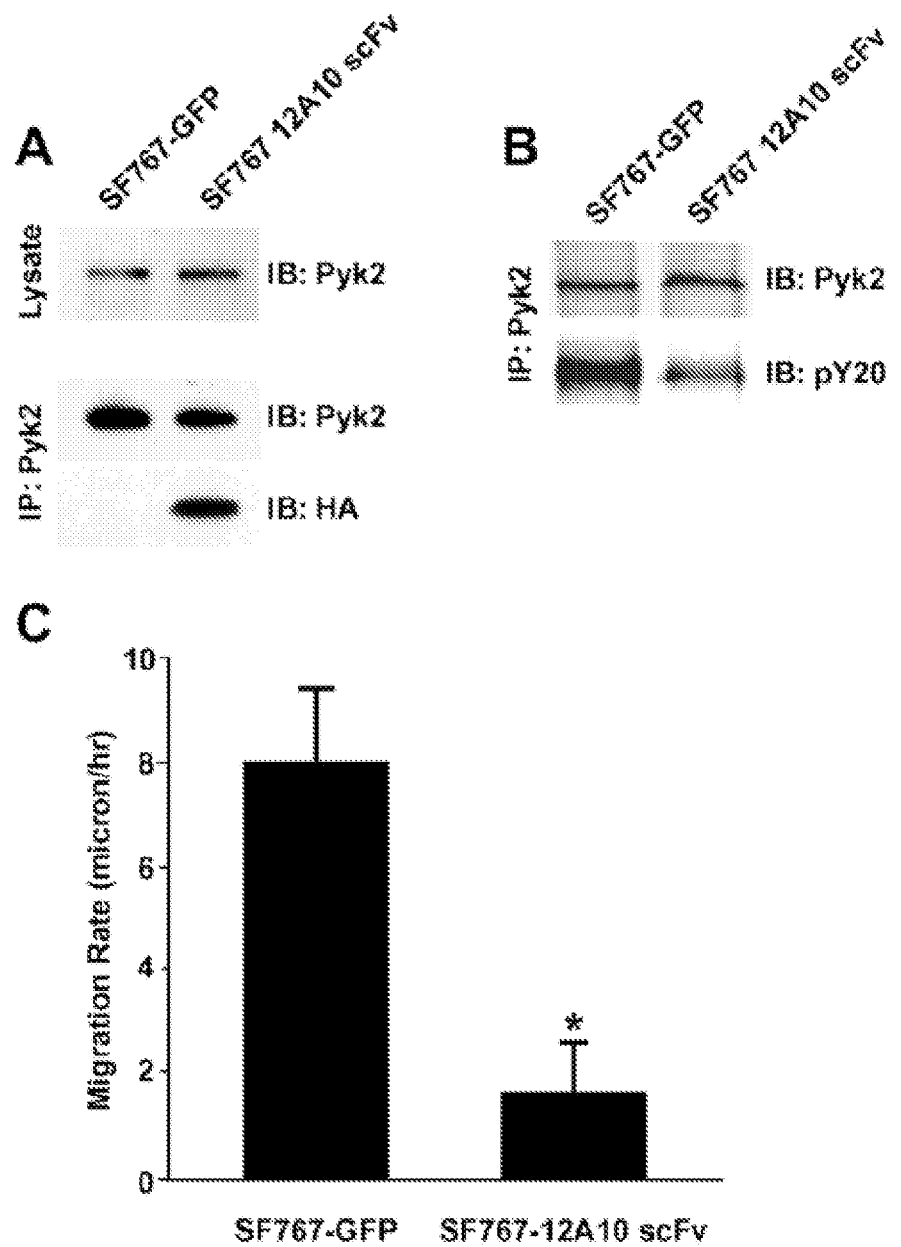
FIG. 5. The 12A10 scFv reacts intracellularly with Pyk2, reduces Pyk2 phosphorylation, and inhibits glioma cell migration. A. Whole cell lysates of SF767-GFP control cells or SF767-12A10 scFv cells were immunoblotted with anti-Pyk2 monoclonal antibody (top panel). Lysates of SF767 control cells or SF767-12A10 scFv cells were immunoprecipitated with the polyclonal anti-Pyk2 antibody, and the precipitates blotted with the anti-Pyk2 monoclonal antibody (middle panel). The blots were stripped and reprobed with the anti-HA antibody to demonstrate that the 12A10 scFv was associated with endogenous Pyk2 (bottom panel). B. Lysates of SF767-GFP control cells or SF767-12A10 scFv cells were immunoprecipitated with polyclonal anti-Pyk2 antibody, and the precipitates immunoblotted with the anti-phosphotyrosine antibody pY20. Blots were stripped and reprobed with anti-Pyk2 antibody to verify equal amounts of Pyk2 in the immunoprecipitate. C. Radial migration assay of SF767-GFP and SF767-12A10 scFv cells on 10 µg/mL laminin. *=p<0.05.

SF767-GFP control cells or SF767 cells stably expressing 12A10 scFv were generated by lentiviral transduction and collected by mass sorting on a flow cytometer. Intracellular expression of the 12A10 scFv did not alter cell growth as cell cycle analysis indicated that the percentage of SF767-12A10 scFv in S-phase was not different than that of the control SF767 cells (31.41±0.28 vs. 32.46±1.49 respectively, p=0.38). In addition, immunoblotting of whole cell lysates indicated that expression of the 12A10 scFv did not alter endogenous Pyk2 expression (FIG. 5A).

Figure 4:
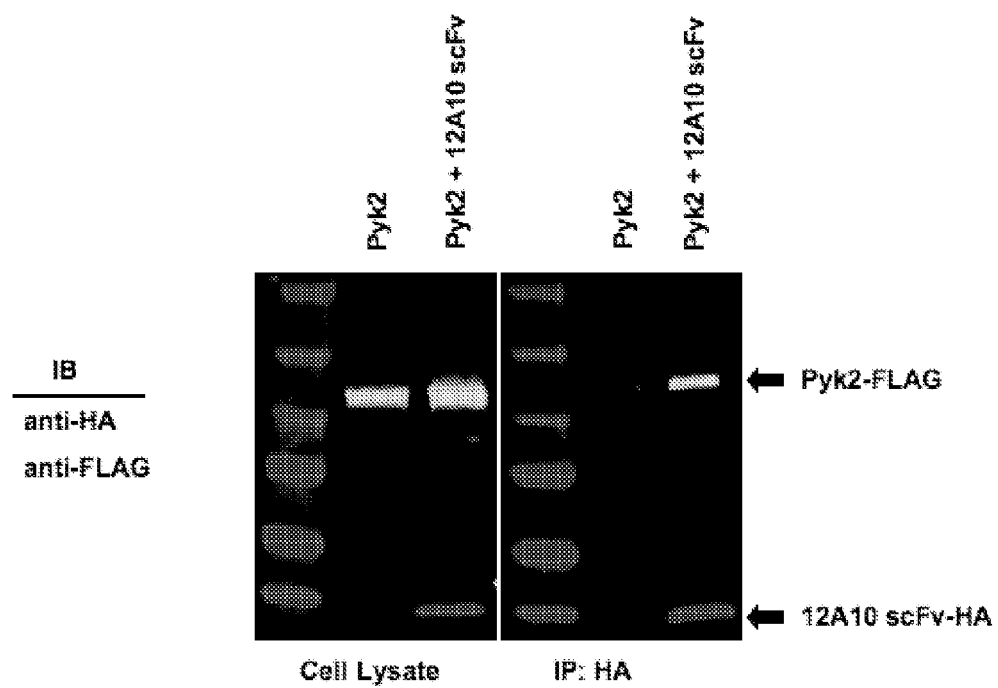
FIG. 4 is a photograph of a Western blot indicating that the 12A10 scFv reacts intracellularly with Pyk2. SF767 glioma cells were transfected with FLAG epitope tagged Pyk2 or co-transfected with FLAG tagged Pyk2 and 3× HA-epitope tagged 12A10 scFv. Cell lysates (left panel) or anti-HA immunoprecipitates (right panel) were immunoblotted with anti-HA and anti-FLAG monoclonal antibodies.

To determine whether the 12A10 scFv retained its capacity to interact with Pyk2 intracellularly, immunoprecipitation experiments were performed. Control SF767 cells or SF767-12A10 scFv cells were lysed, the endogenous Pyk2 immunoprecipitated with anti-Pyk2 antibodies, and the immunoprecipitates probed for the presence of the 12A10 scFv. As shown in FIG. 5A, 12A10 scFv was co-immunoprecitated with Pyk2 indicating that the 12A10 scFv retained its capacity to bind to Pyk2 in the intracellular environment. See, also, FIG. 4. To determine the effect of 12A10 scFv expression on Pyk2 activity, Pyk2 was immunoprecipitated from SF767 GFP and SF767-12A10 scFv cells, and the immunoprecipitates blotted with the anti-phospho tyrosine antibody pY20. There was a 57% reduction in Pyk2 phosphorylation in the SF767-12A10 scFv cells relative to the control cells (FIG. 5B). That a comparable amount of Pyk2 was present in the immunoprecipitates was verified by reprobing the blots with and anti-Pyk2 antibody. Next, the effect of 12A10 scFv expression on glioma cell migration was tested. Intracellular expression of the 12A10 scFv significantly inhibited the migration of SF767 12A10 scFv relative to the migration of control SF767 cells transduced with vector alone (FIG. 5C).

Figure 6:
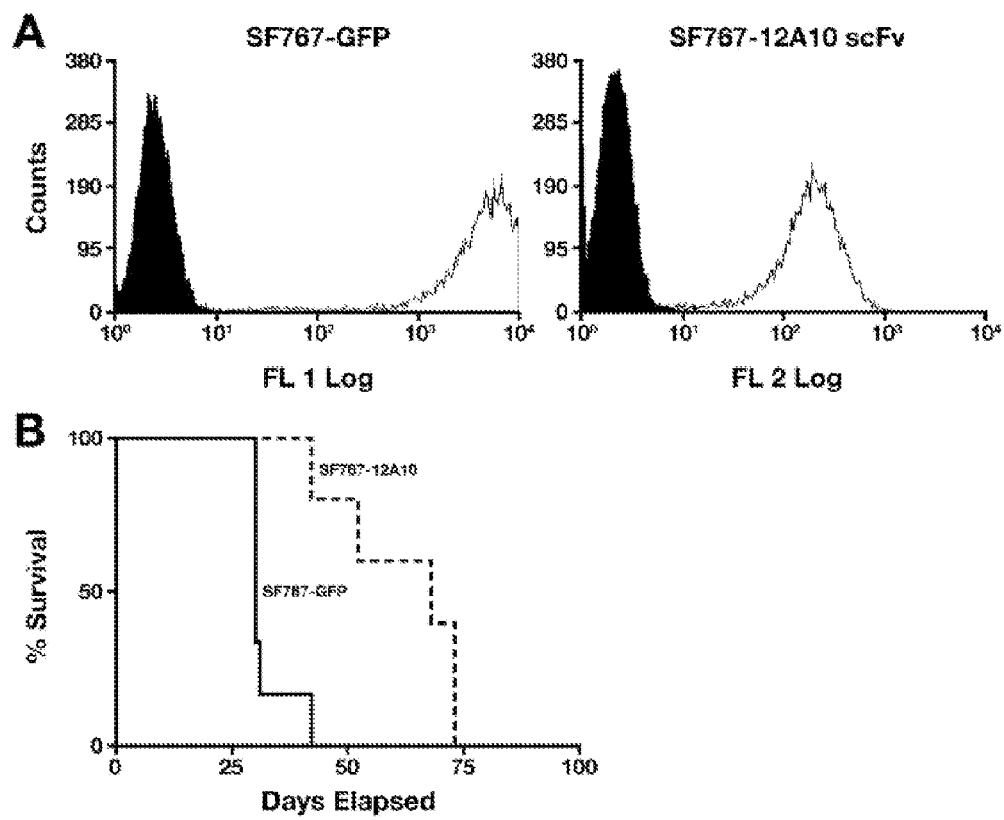
FIG. 6 provides data that 12A10 scFv expression increases survival in an intracranial xenograft model. Control SF767 cells expressing GFP or SF767 cells expressing 12A10 scFv along with dsRed were generated by lentiviral transduction. A. FACS histograms of mass sorted populations with cell number on the ordinate and fluorescence intensity of the abcissa. B. Survival curves of athymic nude mice with intracranial xenografts of SF767-GFP or SF767-12A10 scFv cells. Survival curves show a significant survival benefit for the mice with SF767 12A10 scFv xenografts (p=0.0014).

Expression of 12A10 scFv extends survival of orthotopic xenograft mice. To examine the effect of targeting the Pyk2 FERM domain on tumor progression in vivo, SF767 glioma cells with stable expression of the 12A10 scFv were generated by transduction with a lentiviral construct encoding the 12A10 scFv and red fluorescent protein. SF767 control cells were transduced with the same lentiviral vector expressing only GFP. Transduced cells were mass sorted on a flow cytometer (FIG. 6A), and positive cells were intracranially implanted into nude mice. Mice with xenografts established with control SF767 cells survived a mean of 30 days (FIG. 6B). In contrast, the mean survival duration for the mice with xenografts established with SF767 cells expressing the 12A10 scFv was 68 days, which was significantly longer than the control group (p=0.0014). One mouse developed an unrelated abdominal distention due to an intestinal obstruction and was euthanized on day 34. Two mice developed neurological symptoms consistent with those related with tumor burden and were sacrificed at days 42 and 68. The remaining mice remained healthy without demonstrating any neurological symptoms requiring euthanasia and were sacrificed on day 73. Brains obtained from mice were paraffin-embedded, sectioned, and stained for gross inspection for tumor. Brain slices from the 42-day SF767 12A10 scFv survivor mouse had observable tumor cells, whereas the remaining 73-day survival SF767 12A10 scFv mice had no gross observable tumor burden.

Figure 7:
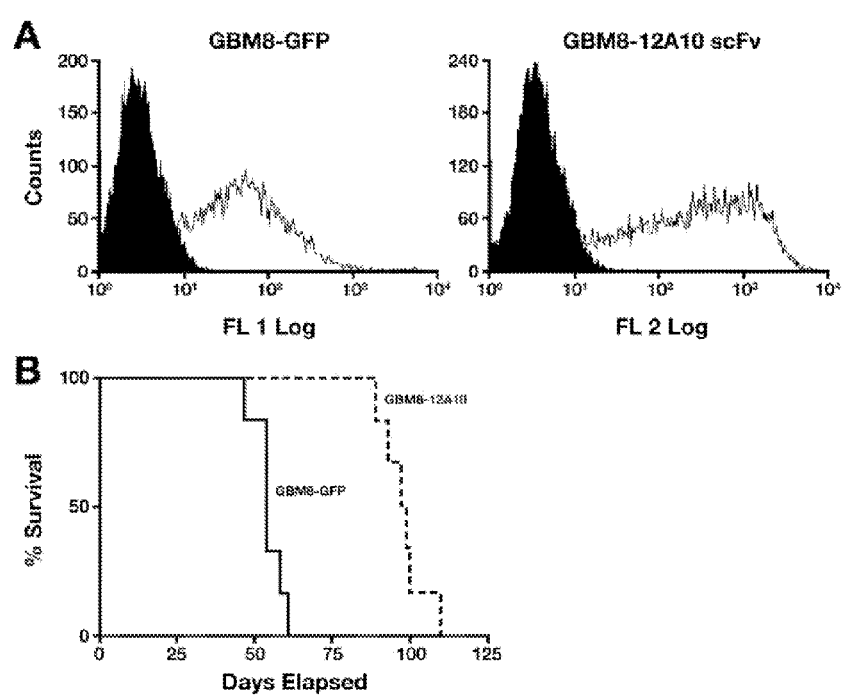
FIG. 7 provides data that 12A10 scFv expression increases survival of mice with primary GBM cell xenografts. Control GBM8 cells expressing GFP or GBM8 cells expressing 12A10 scFv along with dsRed were generated by lentiviral transduction. A. FACS histograms of mass sorted populations. B. Survival curves of athymic nude mice with intracranial xenografts of GBM8-GFP or GBM8-12A10 scFv cells. Mice with GBM8-12A10 xenografts exhibited a significant survival benefit relative to mice with control GBM8 xenografts (p=0.0005).

To substantiate the results obtained with the SF767 glioma cell line, the effect of intracellular expression of the 12A10 scFv on survival of mice with intracranial xenografts established with a primary glioblastoma xenograft cell line GBM8 was examined. GBM8 is from a panel of serially propagated GBM xenografts shown to maintain the morphologic and molecular characteristics of the corresponding patient tumor (Giannini et al., *Neuro-Oncol.*, 7:164-76 (2005) and Park et al., *J. Biol. Chem.*, 279:33315-22 (2004)). Control GBM8 cells and GBM8-12A10 scFv were established by lentiviral transduction, and transduced cells were mass sorted on a flow cytometer (FIG. 7A). Consistent with the results obtained with the SF767 cell line, mice with GBM8-12A10 scFv xenografts survived a mean of 98 days (FIG. 7B), which was significantly longer than control transduced GBM8 cells that survived a mean of 54 days (p=0.0005).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A substantially pure antibody having binding affinity for an F3 subdomain of a Pyk2 polypeptide, wherein said F3 subdomain is amino acid residues 263 to 357 of a human Pyk2 polypeptide, and wherein said antibody is a single chain antibody, a monoclonal antibody, or an antibody fragment.

2. The antibody of claim 1, wherein said antibody is an antibody fragment.

3. The antibody of claim 2, wherein said antibody fragment is an Fab, F(ab')2, or Fv antibody fragment.

4. The antibody of claim 1, wherein said antibody has less than $10^4$ $mol^{-1}$ binding affinity for a tyrosine kinase FAK polypeptide.

5. The antibody of claim 1, wherein said antibody is monoclonal.

6. The antibody of claim 1, wherein said antibody is a single chain antibody.

7. The antibody of claim 6, wherein said antibody comprises the amino acid sequence set forth in SEQ ID NO:1.

8. The antibody of claim 1, wherein said antibody comprises the binding characteristics of a single chain antibody having the amino acid sequence set forth in SEQ ID NO:1.

9. The antibody of claim 1, wherein said antibody is a human antibody.

10. The antibody of claim 1, wherein said antibody is a humanized antibody.

11. The antibody of claim 1, wherein said antibody binds to a wild type Pyk2 FERM domain and does not bind to a Pyk2 FERM domain comprising I308E.

* * * * *